United States Patent
Cai et al.

(10) Patent No.: US 9,398,804 B2
(45) Date of Patent: Jul. 26, 2016

(54) ORAL CARE IMPLEMENT HAVING RESERVOIR FOR DISPENSING ACTIVE AGENT

(75) Inventors: Heng Cai, Skillman, NJ (US); Thomas J. Boyd, Metuchen, NJ (US)

(73) Assignee: COLGATE-PALMOLIVE COMPANY, New York, NY (US)

( * ) Notice: Subject to any disclaimer, the term of this patent is extended or adjusted under 35 U.S.C. 154(b) by 940 days.

(21) Appl. No.: 11/457,086

(22) Filed: Jul. 12, 2006

(65) Prior Publication Data

US 2007/0154863 A1 Jul. 5, 2007

Related U.S. Application Data

(60) Provisional application No. 60/698,594, filed on Jul. 12, 2005.

(51) Int. Cl.

| | | |
|---|---|---|
| *A61C 5/04* | (2006.01) | |
| *A46B 15/00* | (2006.01) | |
| *A46B 11/00* | (2006.01) | |
| *A61K 8/02* | (2006.01) | |
| *A61K 8/22* | (2006.01) | |
| *A61K 8/24* | (2006.01) | |
| *A61K 8/49* | (2006.01) | |
| *A61Q 11/00* | (2006.01) | |

(52) U.S. Cl.
CPC ......... *A46B 15/0002* (2013.01); *A46B 11/0058* (2013.01); *A46B 11/0062* (2013.01); *A46B 11/0065* (2013.01); *A46B 15/0034* (2013.01); *A61K 8/02* (2013.01); *A61K 8/22* (2013.01); *A61K 8/24* (2013.01); *A61K 8/4926* (2013.01); *A61Q 11/00* (2013.01); *A46B 2200/1066* (2013.01)

(58) Field of Classification Search
CPC ............... A46B 2200/1066; A46B 2200/1073; A46B 2200/108; A46B 2200/1086; A46B 2200/1093; A61C 5/062
USPC .......... 433/80–85, 88–90, 216; 15/22.1, 22.2, 15/167.1; 222/641, 639, 645, 646, 649; 132/311, 322, 112–116; 239/62
See application file for complete search history.

(56) References Cited

U.S. PATENT DOCUMENTS

| | | | |
|---|---|---|---|
| 3,810,479 A | 5/1974 | Miles | |
| 4,023,580 A | 5/1977 | Pieters | |
| 4,865,481 A | 9/1989 | Scales | |
| 4,921,150 A * | 5/1990 | Lagergren et al. | 222/639 |

(Continued)

FOREIGN PATENT DOCUMENTS

| | | |
|---|---|---|
| GB | 1210813 | 11/1970 |
| SU | 1417859 | 8/1988 |

(Continued)

OTHER PUBLICATIONS

International Search Report and Written Opinion in Internation Application No. PCT/US06/026904, mailed Nov. 17, 2006.

*Primary Examiner* — Yogesh Patel

(57) ABSTRACT

An oral care implement includes a reservoir containing at least one active agent. The implement has an activator for activating a delivery device which delivers a predetermined amount of an active agent to one or more outlets. A wide variety of types of active agents can be administered at appropriate and accurate doses for therapeutic, hygienic, and/or other benefits.

31 Claims, 1 Drawing Sheet

(56) References Cited

U.S. PATENT DOCUMENTS

| | | | |
|---|---|---|---|
| 5,304,009 A | 4/1994 | Marshall | |
| 5,340,581 A | 8/1994 | Tseng et al. | |
| 5,427,870 A | 6/1995 | Joshi et al. | |
| 5,567,287 A | 10/1996 | Joshi et al. | |
| 5,769,553 A | 6/1998 | Chaudhri et al. | |
| 5,785,956 A | 7/1998 | Sullivan et al. | |
| 5,829,976 A * | 11/1998 | Green | 433/89 |
| 5,851,551 A | 12/1998 | Tseng et al. | |
| 5,865,195 A | 2/1999 | Carter | |
| 5,921,251 A | 7/1999 | Joshi | |
| 5,924,159 A * | 7/1999 | Haitin | 15/105 |
| 5,951,538 A * | 9/1999 | Joshi et al. | 604/500 |
| 5,967,152 A | 10/1999 | Rimkus | |
| 5,971,722 A * | 10/1999 | Maget et al. | 417/379 |
| 5,974,614 A * | 11/1999 | Ross | 15/22.2 |
| 6,045,055 A * | 4/2000 | Joshi et al. | 239/6 |
| 6,108,850 A | 8/2000 | McLaughlin | |
| 6,125,136 A | 9/2000 | Jones et al. | |
| 6,135,126 A | 10/2000 | Joshi | |
| 6,138,315 A | 10/2000 | Schmitt et al. | |
| 6,338,751 B1 | 1/2002 | Litkowski et al. | |
| 6,343,400 B1 | 2/2002 | Massholder et al. | |
| 6,412,137 B1 * | 7/2002 | Heidari | 15/105 |
| 6,427,870 B2 | 8/2002 | De Laforcade | |
| 6,526,991 B2 | 3/2003 | Bodwalk | |
| 6,575,961 B2 | 6/2003 | Joshi | |
| 6,629,969 B2 | 10/2003 | Chan et al. | |
| 6,648,641 B1 * | 11/2003 | Viltro et al. | 433/80 |
| 6,669,390 B1 | 12/2003 | Porter et al. | |
| 6,669,930 B1 | 12/2003 | Hoic et al. | |
| 6,754,928 B1 * | 6/2004 | Rosen | 15/105 |
| 6,770,266 B2 | 8/2004 | Santarpia, III et al. | |
| 6,902,337 B1 * | 6/2005 | Kuo | 401/188 R |
| 2001/0002228 A1 | 5/2001 | Owens | |
| 2003/0194678 A1 * | 10/2003 | Viltro et al. | 433/80 |
| 2003/0221270 A1 * | 12/2003 | Kuo | 15/29 |
| 2003/0224320 A1 | 12/2003 | Kandelman et al. | |
| 2004/0019990 A1 | 2/2004 | Farrell | |
| 2004/0134000 A1 * | 7/2004 | Hilfinger et al. | 15/22.1 |
| 2004/0134010 A1 | 7/2004 | Tseng et al. | |
| 2004/0261790 A1 | 12/2004 | Joshi et al. | |
| 2005/0023371 A1 | 2/2005 | Joshi et al. | |
| 2005/0026103 A1 * | 2/2005 | Wasylucha | 433/29 |
| 2005/0238412 A1 * | 10/2005 | Jacobs et al. | 401/270 |
| 2006/0019214 A1 * | 1/2006 | Lawrence et al. | 433/29 |
| 2007/0154863 A1 | 7/2007 | Cai et al. | |

FOREIGN PATENT DOCUMENTS

| | | |
|---|---|---|
| WO | 0241802 A | 5/2002 |
| WO | WO2004026077 A1 * | 4/2004 |

* cited by examiner

ORAL CARE IMPLEMENT HAVING RESERVOIR FOR DISPENSING ACTIVE AGENT

CROSS-REFERENCE TO RELATED APPLICATIONS

This application claims the benefit of priority to U.S. Patent Application No. 60/698,594, filed Jul. 12, 2005 in which the contents are incorporated by reference herein.

FIELD OF THE INVENTION

The present invention is directed to an oral care implement having a reservoir for dispensing an active agent.

BACKGROUND OF THE INVENTION

Many currently available toothpastes contain auxiliary agents for tooth whitening or other hygienic purposes in addition to tooth cleaning. Although many types of agents can be effectively incorporated into toothpastes, the ability to incorporate auxiliary components into toothpastes is limited by such factors as the compatibility of the components with the toothpaste and possible deleterious effects the components and the toothpaste may have on each other. For example, a reactive component may become neutralized prior to use, or may adversely affect the shelf life, viscosity, taste, or other properties of the toothpaste.

U.S. Pat. No. 6,135,126 to Joshi, incorporated herein by reference, discloses a toothbrush having an electrochemical cell for generating an oxidizing gas via an internal electrochemical process. During brushing, a user engages a switch to activate an internal electrochemical cell which generates the oxidizing agent, such as oxygen. The oxidizing gas is exhausted to the bristle portion of the brush for application to the user's oral cavity. Other gaseous products generated in the electrochemical cell, such as hydrogen, are directed away from the bristle portion of the brush. This arrangement has inherent drawbacks.

There remains a need for an improved oral care implement having the ability to deliver beneficial agents using an oral care implement without suffering from drawbacks and limitations known in the art.

SUMMARY OF THE INVENTION

The present invention is directed to an oral care implement having a reservoir containing at least one active agent.

The oral care implement has a delivery device actuator, such as a switch, for activating a delivery device, such as a pump, which delivers a predetermined amount of a substance, such as an active agent, to one or more outlets, which can be located in the vicinity the tooth cleaning elements, e.g., bristles, and/or other portion(s) of the oral care implement. A wide variety of active agents can be administered at appropriate and accurate doses for therapeutic, hygienic, and/or other benefits, such as fresh breath, tooth whitening, reducing sensitivity of the teeth or producing sensations of heat, cool, or tingling.

The oral care implement advantageously can be manufactured at relatively low cost, is easy to use, and can deliver a predetermined quantity of an active agent upon a user activating a switch.

BRIEF DESCRIPTION OF THE DRAWINGS

The objects, features, and advantages of the invention will be apparent from the following more detailed description of certain embodiments of the invention and as illustrated in the accompanying drawings in which.

DETAILED DESCRIPTION OF THE INVENTION

Figure 1:
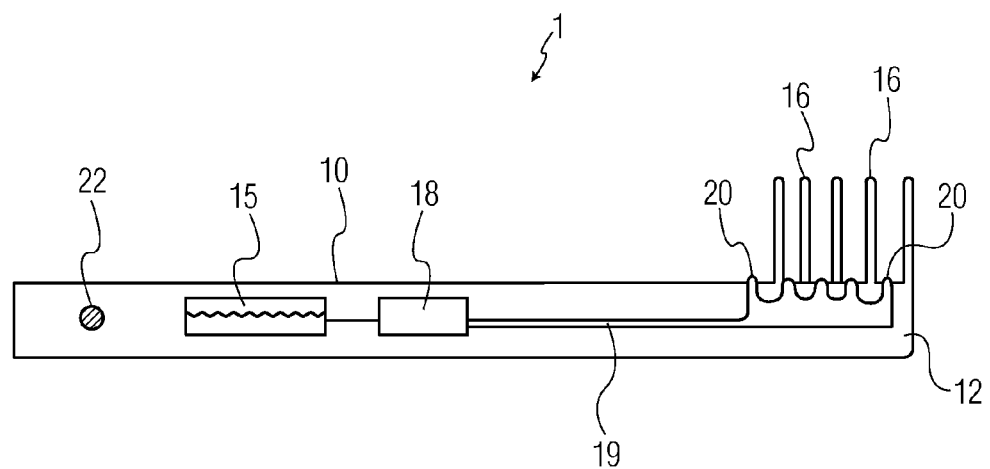
FIG. 1 is a schematic illustration of a toothbrush according to one embodiment of the invention.

FIG. 1 schematically illustrates a toothbrush 1 having a handle 10 and a head 12 containing tooth cleaning elements, such as bristles 16 and/or elastomeric cleaning elements (not shown) or the like. A storage location, such as a reservoir 15, is provided within the handle 10 for storing the active agent. The handle 10 or other exterior portion of the toothbrush 1 preferably contains a delivery device actuator or switch, such as a user-actuated button 22, for activating a delivery device such as pump 18. The pump 18 can be located before or after the reservoir 15. Upon pressing the button 22, the pump 18 causes a predetermined quantity of a medium preferably containing an active agent to be delivered from the reservoir 15 through a channel 19 leading to a plurality of outlets 20.

As shown in FIG. 1, the outlets 20 may be located on the surface of the head 12 between or in the vicinity of the bristles 16. Alternatively, the outlets 20 may be located on other portions of the head 12, handle 10, or elsewhere on the toothbrush 1. Alternatively, the active agent may be delivered through the bristles 16, such as if the bristles comprised hollow lumens or the like. In this arrangement, the tip of the bristles made have at least one aperture for releasing the active agent. Alternatively, the active agent can also be delivered simultaneously through outlets 20 located at different portions of the toothbrush 1, for example to aid in the application of the active agent to different areas of the mouth. Although a plurality of outlets 20 is illustrated, it is contemplated that a single outlet could be used.

The switch for activating the pump 18 may be a button 22, as illustrated in FIG. 1, or may be another type of switch such as a user-activated toggle switch or rotating dial. Depressing the button 22 preferably activates a timing circuit which causes the pump 18 to operate for an interval needed to pump a predetermined amount of the medium containing the active agent from the reservoir 15 and through the outlets 20. The pump is connected to a power source or has a power source, such as a battery (not shown). The timing circuit causes the pump 18 to operate for an interval of time which either may be preset or may be adjustable, e.g., by a user-activated rotating dial, which may vary depending on the active agent and the desired delivery regimen. While an external switch 22 has been described, it will be appreciated that a user-operated, internal switch that activates the delivery device upon the mechanical action of brushing, is also contemplated.

Figure 2:
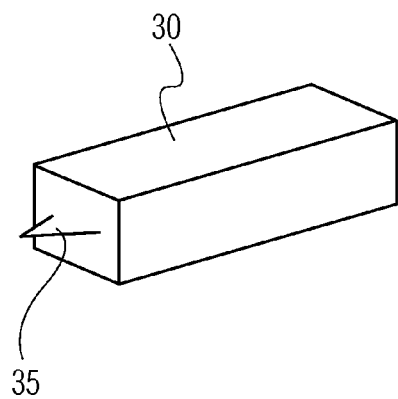
FIG. 2 schematically illustrates a replaceable cartridge in accordance with another embodiment of the invention.

The medium containing the active agent can be incorporated into a sealed reservoir 15 during manufacture of the toothbrush 1, in which case the toothbrush 1 can be disposed of after the supply of the active agent is exhausted. Alternatively, the reservoir 15 can be refillable through an inlet (not shown), or can be replaceable, e.g., by inserting a replaceable cartridge into a recess in the toothbrush or toothbrush handle 10. FIG. 2 schematically illustrates an example of a replaceable cartridge 30. The cartridge can have a sharpened element 35 which penetrates a membrane in the recess of the toothbrush to permit the medium to flow from the cartridge 30 into the channel 19. The cartridge 30 can be spring-loaded to stay in place after insertion into the recess, and can have a seal to prevent unwanted leakage of the active agent. The cartridge 30 can be disposable or refillable. Other methods of providing a refillable and/or replaceable cartridge or the like are contemplated.

Optionally, a user-activated switch, such as a dial (not shown), can have multiple settings for selecting one of several active agents. For example, the dial can have a first setting for oxidizer/whitener treatment, a second setting for breath freshener treatment, and a third setting for antimicrobial treatment. The dial setting instructs the timing circuit to activate the pump 18 for a time interval appropriate for the selected active agent.

In one embodiment, a kit comprises a toothbrush and at least one cartridge containing an active agent. A user may select among multiple cartridges for a desired treatment. If the active agents have different intervals of application, the toothbrush can be provided with a dial, as previously described, to enable the user to select the appropriate setting. Similarly, a single cartridge can come pre-loaded with multiple active agents that can be selectively accessed and delivered by a switch or the like. The kit can also include a dentifrice if desired.

The predetermined amount can be suitably selected to deliver an accurate dose of the active for its intended purpose. The amount can be controlled by controlling the duration the pump 18 operates after the button 22 is pressed. The duration of dispensation will depend on the desired dose and the flow-rate of the medium, and typically ranges from about 1 second to 5 minutes, often from about 5 seconds to about 2 minutes, and preferably ranges from about 10 seconds to 30 seconds. The timing of the dispensing action can be either right after the button 22 is pressed, or at a delay programmed as desired.

Any suitable pump can be used for delivering the medium from the reservoir 15 to the outlets 20. Suitable devices are commercially available, such as the gas-generating cell or microcell technology available from Microlin Technology/Ceramatec Inc. Reference also is made to U.S. Pat. Nos. 6,135,126, 6,575,961, 6,045,055, 5,427,870, and 5,567,287, and published application U.S. 2005/0023371 A1, the disclosures of which are hereby incorporated by reference as alternative pump arrangements useable in the toothbrush. The pump may deliver the medium through a variety of different actions that are mechanical, electrical, chemical or a combination thereof, depending on the pump structure. For example, the gas-generating cell available from Microlin Technology employs a piston-cylinder type of arrangement.

Advantageously, the active agent itself can be contained in the reservoir 15. In other words, it is not necessary to generate the active agent internally or in situ. This simplifies the construction of the toothbrush and avoids the need to handle any byproducts associated with the synthesis of the active agent. Alternatively, an agent in one reservoir can be delivered via a delivery device to another reservoir where it is "activated," where it is then delivered via another delivery device to the one or more outlets. This type of delivery system, employing multiple connections that are direct or indirect, is also contemplated within the scope of the present invention.

In FIG. 1, a toothbrush 1 is shown schematically having a head 12, bristles 16, and a handle 10. It should be understood that any bristle configuration and any handle configuration can be used, and the present invention should not be regarded as being limited to any particular configuration. The outlet(s) 20 preferably are located in the bristle region on the bristle side of the head of the toothbrush, for example between or interspersed with bristles 16. Alternatively, the outlet(s) 20 can be located on the side of the head opposite the bristles, or on the side edges of the head, or on a combination of sides as desired. Alternatively, the outlet(s) 20 can be located adjacent the head or in the region of the head, but not actually on the head.

The toothbrush 1 can be used by applying toothpaste to the bristles 16 and brushing the teeth in a conventional manner. A predetermined amount of the active agent is administered by activating the switch, e.g., depressing button 22, to activate the pump 18, which causes the medium containing the active agent to be delivered though the outlets 20. The switch instructs the timing circuit to activate the pump 18 for a predetermined time, which in turn dispenses the active agent in a predetermined dose through the outlets 20. The active agent can be then applied to the teeth of a user using bristles 16 via the outer surface of the bristles 16. Nevertheless, in another arrangement, the active agent can be applied teeth via a lumen within the bristle 16, instead of outlet 20. The active agent can be administered before, during, or after brushing.

Non-limiting examples of active agents which can be used include antibacterial agents, such as chlorhexidine, cetyl pyridininum chloride, triclosan, zinc salts, and magnolia extract; anti-attachment agents, such as ethyl lauroyl arginine HCl; oxidative or whitening agents, such as hydrogen peroxide, urea peroxide, sodium percarbonate, and $PVP-H_2O_2$; anti-cavity agents, such as sodium fluoride, sodium monofluorophosphate, stannous fluoride; supercharged fluoride delivery ingredients (such as dicalcium phosphate dihydrate and others disclosed in U.S. Pat. No. 5,785,956); tooth sensitivity ingredients, such as $KNO_3$, stannous fluoride, sodium silicate, and bioactive glass (such as those disclosed in U.S. Pat. No. 6,338,751); gum health actives, including those which reduce inflammation pathways and/or interfere in bacterial processes which produce inflammatory stimuli, such as Univestin (Unigen Pharma), bachalin, polyphenols, ethyl pyruvate, green tea extracts, rosemary extracts and other herbal extracts, and guanidinoethyl disulfide; nutritional type ingredients, such as vitamins, minerals, amino acids, vitamin E, and folic acid; tartar control or anti-stain ingredients, including phosphate salts, polyvinylphosphonic acid, PVM/MA copolymer; enzymes, such as those used for plaque disruption; sensate ingredients, such as those providing cooling (such as menthol), tingle, or heat sensations (such as capsaicin or capsicum oil); flavors and flavor ingredients; colorants or other aesthetic agents; and combinations thereof Examples of flavors and flavor ingredients include essential oils, menthol, carvone, and anethole, and various flavoring aldehydes, esters, and alcohols. Examples of essential oils include oils of spearmint, peppermint, wintergreen, sassafras, clove, sage, eucalyptus, marjoram, cinnamon, lemon, lime, grapefruit, and orange.

The active agent and/or its medium can be selected to complement the toothpaste formula, such as by coordinating flavors, colors, aesthetics, or active ingredients. A flavor can be administered to create a gradual flavor change during brushing, which presently is not possible using toothpaste alone. The flavor changes described here along with other changes in sensation can also be used as a signal for indicating that an effective brushing routine is complete. A colorant can be added to create a color change during use. Flavor and/or color can also be used to signal another benefit, such as tooth whitening or anti-bacterial action.

The active agent may be compatible with toothpaste, or may be unstable and/or reactive with typical toothpaste ingredients. Non-limiting examples of components which tend to be unstable and/or reactive with typical toothpaste ingredients include hydrogen peroxide, sodium fluoride (reacts with calcium or zinc salts), various calcium salts (reacts with sodium fluoride), and cationic ingredients, such as cetyl pyridinium chloride, chlorhexidiene, and ethyl lauroyl arginine HCl (react with SLS, other anionic ingredients, and many silica abrasives). The active agent also may be a tooth cleaning agent to boost the overall efficacy of brushing. Such tooth cleaning agents may or may not be compatible with the toothpaste ingredients.

The active agent can be provided in any suitable vehicle, such as in an aqueous solution or a non-aqueous solution or an oil or in the form of gel or paste or an emulsion or a multiple emulsion or a liquid crystal gel. The vehicle can have a variety of different visual aesthetics including clear solution or gel or opaque solution or gel. Non-limiting examples of vehicles include water, monohydric alcohols such as ethanol, poly (ethylene oxides) such as polyethylene glycols such as PEG 2M, 5M, 7M, 14M, 23M, 45M, and 90M available from Union Carbide, carboxymethylene polymers such as Carbopol® 934 and 974 available from B. F. Goodrich, and combinations thereof. The selection of a suitable vehicle will be apparent to persons skilled in the art depending on such factors as the properties of the active agent and the desired properties of the medium, such as viscosity. Examples of tooth whitening compositions are described in U.S. Pat. Nos. 6,770,266 and 6,669,930, the disclosures of which are hereby incorporated by reference.

The predetermined quantity of the medium dispensed may vary over a wide range depending on such factors as the identity of the active agent and its concentration in the medium. The quantity dispensed usually ranges from about 1 to about 100 µL per use, more usually from about 5 to about 50 µL. For example, the pump 18 can be configured to deliver 10 µL of 20% cetylpyridinium chloride gel over a period of 30 seconds, e.g., for application during the first 30 seconds of brushing the teeth. An advantage of this delivery is that ingredients incompatible with the toothpaste are exposed to the toothpaste as little as possible.

The reservoir can contain a quantity of the active agent medium intended for a single use or a small number of uses, or may facilitate repeated use over an extended period of time, e.g., up to several months or several years (if used with a toothbrush having a replaceable head for example). The size of the reservoir can be selected to be compatible with the desired overall dimensions of the toothbrush 1 as well as such factors as the stability of the active agent and the quantity of medium administered during each application.

The supply of active agent in the reservoir 15 preferably is free or substantially free of components which are incompatible with the active agent and/or the medium containing the active agent, such as incompatible toothpaste components as previously identified. In the preferred practice of the invention, the reservoir 15 is free or substantially free of toothpaste, as toothpaste is separately applied to the bristles 16 by the user. Alternatively as noted above, an active agent may be originally retained in one reservoir and then transferred to another reservoir where it is activated just prior to delivery, which may be useful in certain conditions or circumstances.

The toothbrush 1 can be equipped with a light source, such as an ultraviolet (UV) or infrared (IR) light. The light source can be used to enhance tooth cleaning or whitening by itself and/or by activating the active agent and/or ingredients in the toothpaste. The toothbrush 1 can have a secondary switch (not shown) for activating the light source. An example of a toothbrush having a UV light source for activating a photoactivatable material for tooth cleaning is described in U.S. Pat. No. 6,343,400 to Massholder et al. The back of the toothbrush 1 can be equipped with a special surface for polishing teeth with (silica) toothpaste. Non-limiting examples of such a surface include rubber, elastomer, woven fabric or wool.

The toothbrush 1 optionally can be provided with compartments and/or access panels for access to the various components, such as the power source and reservoir. The power source can be, for example, a replaceable or rechargeable battery as well known.

The following examples are provided for illustrative purposes only and should not be construed as limiting the scope of the present invention.

Example 1

Table I illustrates a cetylpyridinium chloride concentrate that is dispensed from a toothbrush reservoir during brushing as an antibacterial agent.

TABLE I

| Ingredient | Wt % |
|---|---|
| Carbopol 974P | 1–2 |
| PEG 600 | 10 |
| FD&C blue #1(1% | 0.5 |
| Cetylpyridinium chloride | 20 |
| Water | Q.S. |

Example 2

Table II shows a hydrogen peroxide solution that is dispensed from a toothbrush reservoir during brushing as a whitening booster.

TABLE II

| Ingredient | Wt % |
|---|---|
| Carbopol 974P | 1–2 |
| Hydrogen peroxide | 30 |
| Water | Q.S. |

Example 3

Table III illustrates a hydrogen peroxide gel which that is dispensed from a toothbrush reservoir during brushing as a whitening liquid. The gel also can be applied post-brushing for tooth whitening.

TABLE III

| Ingredient | Wt % |
|---|---|
| Water | 10.07 |
| Carbopol 974 | 1.00 |
| 95% Ethyl alcohol | 34.8 |
| Glycerin | 5.00 |
| PEG 600 | 10.00 |
| PEG 2M | 14.00 |
| Hydrogen peroxide | 25.00 |
| 85% Phosphoric acid | 0.05 |
| Monobasic sodium phosphate | 0.05 |
| Total | 100.00 |

Example 4

Table IV shows a phosphoric acid solution that is dispensed from a toothbrush reservoir during brushing as a whitening liquid. The solution has a pH of about 4.0.

TABLE IV

| Ingredient | Wt % |
|---|---|
| Purified water | 25.1 |
| Carbopol 974 | 1.00 |
| 95% Ethyl alcohol | 34.8 |
| Glycerin | 5.00 |
| PEG 2M | 15.00 |
| Urea peroxide | 18.00 |
| 85% Phosphoric acid | 0.10 |
| Monobasic sodium phosphate | 1.0 |
| Total | 100.00 |

Example 5

Table V illustrates another hydrogen peroxide solution that is dispensed from a toothbrush reservoir during brushing as a whitening booster. The composition alternatively can be applied to the teeth after brushing as a whitening agent.

TABLE V

| Ingredient | Wt % |
|---|---|
| Carbopol 974P | 1 |
| 95% ethyl alcohol | 34.8 |
| Glycerin | 5 |
| PEG 600 | 10 |
| PEG 2M | 14 |
| 85% phosphoric acid | 0.05 |
| Monobasic sodium phosphate | 0.05 |
| Hydrogen peroxide | 25 |
| Water | Q.S. |

Example 6

Alternative liquid whitening gels are prepared by modifying the base formula of Example 5 by adding either (1) 2 to 5 wt % polyethylene (PE) powder having an average particle size of 6 to 8 microns; (2) 1 to 5 wt % polytetrafluoroethylene (PTFE) powder having particle size of 5 to 6 microns; (3) 0.8 to 2.5 wt % polypropylene (PP) powder having a particle size of 4 to 50 microns; (4) 2 to 5 wt % PE powder and 0.11 to 0.4 wt % titanium dioxide powder having a particle size of 10 to 45 microns. Examples of gels having the polymer and/or inorganic titanium powders incorporated in the base formula are shown in Tables VI and VII.

TABLE VI

| | A (wt %) | B (wt %) | C (wt %) | D (wt %) | E (wt %) | F (wt %) | G (wt %) |
|---|---|---|---|---|---|---|---|
| Base Formula | 99.0 | 98.0 | 95.0 | 98.0 | 95.0 | 99.2 | 97.5 |
| +PE | — | — | — | 2.0 | 5.0 | — | — |
| +PTFE | 1.00 | 2.0 | 5.0 | — | — | — | — |
| +PP | — | — | — | — | — | 0.8 | 2.5 |

TABLE VII

| | GA (wt %) | H (wt %) | I (wt %) | J (wt %) | K (wt %) | L (wt %) |
|---|---|---|---|---|---|---|
| Base Formula | 99.5 | 97.90 | 97.80 | 97.60 | 94.90 | 99.5 |
| +PE | — | 2.00 | 2.00 | 2.00 | 5.00 | — |
| +TiO₂ | — | 0.10 | 0.20 | 0.40 | 0.10 | 0.5 |
| +TiO$_2$ coated mica | 0.5 | — | — | — | — | — |

Example 7

Table VIII shows another exemplary composition of a liquid whitening gel that is dispensed from a reservoir of a toothbrush during brushing as described herein.

TABLE VIII

| Liquid Gel Formula | Wt % |
|---|---|
| Carbomer | 1.00 |
| PEG 600 | 9.96 |
| BHT | 0.03 |
| Glycerin | 4.98 |
| Water | 17.00 |
| Ethyl alcohol | 34.67 |
| PEG 2M | 13.95 |
| $H_2O_2$(35%) | 17.93 |
| Sodium Phosphate | 0.05 |
| Phosphoric acid | 0.05 |
| Titanium dioxide | 0.38 |

Example 8

Table IX example shows the composition of a breath protection gel that is dispensed from a toothbrush reservoir as described herein.

TABLE IX

| Ingredient | Wt % |
|---|---|
| Carbopol 974P | 1 |
| PVM/MA copolymer | 10 |
| Triclosan | 20 |
| Ethyl alcohol | 40 |
| Zinc gluconate | 20 |
| Water | Q.S. |

What is claimed is:

1. An oral care implement comprising:
   a head;
   a reservoir for containing an active agent;
   at least one outlet;
   a pump having a gas-generating cell or microcell for delivering a predetermined amount of the active agent;
   a power source for powering the pump; and
   an activator, wherein the activator is an internal switch that activates the pump in response to mechanical action of brushing with the oral care implement to deliver the predetermined amount of the active agent; and
   wherein the active agent is substantially free of a dentifrice.

2. The oral care implement of claim 1, wherein the head includes a plurality of tooth cleaning elements and wherein the at least one outlet comprises a plurality of outlets in the vicinity of the tooth cleaning elements.

3. The oral care implement of claim 1, wherein the active agent is selected from the group consisting of antibacterial agents; anti-inflammatory agents; anti-attachment agents; oxidative or whitening agents; anti-cavity agents; fluoride delivery ingredients; tooth sensitivity ingredients; gum health actives; nutritional ingredients; tartar control or anti-stain ingredients; enzymes; sensate ingredients; and flavors or flavor ingredients; and surface conditioning agents.

4. The oral care implement of claim 1, wherein the active agent is selected from the group consisting of chlorhexidine, cetyl pyridininum chloride, triclosan, zinc salts, magnolia extract, rosemary extract, green tea, grape, herbal extracts, hydrogen peroxide, urea peroxide, sodium percarbonate, PVP-H2O2, bachalin, polyphenols, ethyl pyruvate, guanidinoethyl disulfide; vitamins, minerals, amino acids, vitamin E, folic acid, phosphate salts, polyvinylphosphonic acid, menthol, carvone, anethole, extracts of spearmint, peppermint, wintergreen, sassafras, clove, sage, eucalyptus, marjoram, cimlamon, lemon, lime, grapefruit, orange, fluoride salts, stannous salts, potassium nitrate, sodium silicate, bioactive glass, and arginine salts.

5. The oral care implement of claim 1, wherein the reservoir comprises a replaceable cartridge.

6. The oral care implement of claim 1, wherein the reservoir further comprises a plurality of active agents selectively deliverable to the at least one outlet.

7. The oral care implement of claim 1, further comprising a light source and a secondary switch for activating the light source.

8. The oral care implement of claim 1 further comprising a timing circuit operably coupled to the activator, the activator activating the timing circuit which causes the pump to operate for an interval of time to dispense the predetermined amount of the active agent from the reservoir and through the at least one outlet.

9. The oral care implement of claim 8 further comprising a user-activated dial that adjusts the interval of time.

10. The oral care implement of claim 8 wherein the interval of time is preset.

11. The oral care implement of claim 1 wherein the gas-generating cell or microcell is electrochemical.

12. A method of administering an active agent using an oral care implement having a head containing tooth cleaning elements, a reservoir containing an active agent, wherein the active agent is substantially free of a dentifrice, at least one outlet for dispensing the active agent, a pump having a gas-generating cell or microcell for delivering a predetermined amount of the active agent from the reservoir to the at least one outlet, a power source for powering the pump, and an activator, the activator being an internal switch activated by mechanical action of brushing, the internal switch operably coupled to the pump, the method comprising:
   brushing an oral cavity with the oral care implement, the internal switch activating the pump in response to the mechanical action of the brushing to dispense the predetermined amount of the active agent from the reservoir through the at least one outlet; and
   applying the active agent to the oral cavity.

13. The method of claim 12, wherein the active agent is applied to the oral cavity during brushing.

14. The method of claim 12, wherein the active agent is selected from the group consisting of antibacterial agents, anti-attachment agents, surface conditioning agents, anti-inflammatory ingredients, oxidative or whitening agents, supercharged fluoride delivery ingredients, tooth sensitivity ingredients, gum health actives, nutritional ingredients, tartar control or anti-stain ingredients, enzymes, sensate ingredients, and flavors or flavor ingredients.

15. The method of claim 12, wherein the active agent is selected from the group consisting of chlorhexidine, cetyl pyridininum chloride, triclosan, zinc salts, magnolia extract, rosemary extract, green tea, grape, herbal extracts, hydrogen peroxide, urea peroxide, sodium percarbonate, PVP-H2O2, bachalin, polyphenols, ethyl pyruvate, guanidinoethyl disulfide; vitamins, minerals, amino acids, vitamin E, folic acid, phosphate salts, polyvinylphosphonicacid, menthol, carvone, anethole, extracts of spearmint, peppermint, wintergreen, sassafras, clove, sage, eucalyptus, marjoram, cinnamon, lemon, lime, grapefruit, orange, fluoride salts, stannous salts, potassium nitrate, sodium silicate, bioactive glass, and arginine salts.

16. The method of claim 12, further comprising the step of providing a plurality of active agents in the reservoir.

17. The method of claim 16, further comprising the step of selecting one of the plurality of active agents to be delivered.

18. The method of claim 16, further comprising the step of dispensing the active agent for a predetermined time that varies by the active agent being dispensed.

19. The method of claim 12, further comprising the step of dispensing the predetermined amount of the active agent for a predetermined time.

20. The method of claim 19, wherein the predetermined time varies by the active agent being dispensed.

21. The method of claim 12, wherein the oral care implement further comprises a timing circuit operably coupled to the activator, wherein the activator activates the timing circuit in response to the mechanical action of brushing which causes the gas generating pump to operate for an interval of time to dispense the predetermined amount of the active agent from the reservoir and through the at least one outlet.

22. The method of claim 21 wherein the oral care implement further comprising a user-activated dial that adjusts the interval of time.

23. The method of claim 21 wherein the interval of time is preset.

24. An oral care implement comprising:
   a head;
   a reservoir for containing an active agent;
   at least one outlet;
   a delivery device for delivering a predetermined amount of the active agent,
   a power source for powering the delivery device;
   an activator operably coupled to the delivery device and the power source, wherein the activator is an internal switch that activates the delivery device in response to mechanical action of brushing with the oral care implement; and
   a timing circuit operably coupled to the activator, wherein upon the activator being activated, the activator activates the delivery device and the timing circuit, the timing circuit causing the delivery device to operate for an interval of time to dispense the predetermined amount of the active agent from the reservoir and through the at least one outlet.

25. The oral care implement of claim 24 wherein the delivery device is a pump having a gas generating cell or microcell.

26. The oral care implement of claim 25 further comprising a user-activated dial that adjusts the interval of time.

27. The oral care implement of 25 wherein the interval of time is preset.

28. An oral care implement comprising:
   a head;
   a reservoir for containing an active agent;
   at least one outlet;
   a delivery device for delivering a predetermined amount of the active agent;
   a power source for powering the delivery device; and
   an activator, wherein the activator is an internal switch that activates the delivery device in response to mechanical action of brushing with the oral care implement to deliver the predetermined amount of the active agent.

29. The oral care implement of claim 28 further comprising a timing circuit operably coupled to the activator, the activator activating the timing circuit which causes the delivery device to operate for an interval of time to dispense the predetermined amount of the active agent from the reservoir and through the at least one outlet.

30. The oral care implement of 29 further comprising a user-activated dial that adjusts the interval of time.

31. The oral care implement of 29 wherein the interval of time is preset.

* * * * *